United States Patent [19]

Haber et al.

[11] Patent Number: 4,810,249
[45] Date of Patent: Mar. 7, 1989

[54] LINEAR AND VERNIER-TYPE SYRINGE

[75] Inventors: Terry M. Haber; Clark B. Foster, both of El Toro, Calif.

[73] Assignee: Habley Medical Technology Corp., Laguna Hills, Calif.

[21] Appl. No.: 25,244

[22] Filed: Mar. 12, 1987

[51] Int. Cl.$^4$ ............................................ A61M 5/315
[52] U.S. Cl. .................................. 604/210; 604/211; 604/224; 604/194; 222/46; 222/390
[58] Field of Search ................................ 604/208–211, 604/224, 194; 222/390, 386, 46

[56]  References Cited

U.S. PATENT DOCUMENTS

| | | | |
|---|---|---|---|
| 949,163 | 2/1910 | Stapley | 222/390 |
| 2,283,915 | 5/1942 | Cole | 604/211 |
| 2,578,394 | 12/1951 | Blackman | 604/194 |
| 3,107,785 | 10/1963 | Roehr | 604/194 X |
| 3,353,718 | 11/1967 | McLay | 604/224 X |
| 4,067,333 | 1/1978 | Reinhardt et al. | 604/194 X |
| 4,189,065 | 2/1980 | Herold | 222/46 |
| 4,583,974 | 4/1986 | Kokernak | 604/211 |

Primary Examiner—Samuel Scott
Assistant Examiner—Allen J. Flanigan
Attorney, Agent, or Firm—Townsend and Townsend

[57] ABSTRACT

A syringe assembly having a cylinder adapted to receive a hypodermic needle at one end thereof and a piston reciprocably movably disposed in the cylinder. The exterior of the piston is at least partially threaded and it includes a longitudinal, exterior groove extending over the length of the thread. The cylinder includes a piston thread engaging section which is integrally constructed, e.g. molded with the cylinder, and hingeable relative to the cylinder so that the thread engaging section can be moved through a cutout in the cylinder into engagement with the piston thread. The cylinder has an integrally constructed collar at its open end and forms a detent that can be resiliently biased against the piston so that upon rotation of the piston about its axis the detent engages the longitudinal groove and thereby generates a signal each time the detent engages the groove, i.e. each time the piston is rotated through a predetermined arc and dispenses a predetermined, measured amount of liquid. An end of the piston has a cavity which receives the needle and frictionally retains it in the cavity during storage and shipment of the syringe assembly. The syringe assembly can be conventionally operated, by linearly reciprocating it, when the thread engaging section disengaged from the piston thread, and by rotating the piston about its axis, when the thread engaging section is in engagement with the piston thread.

51 Claims, 7 Drawing Sheets

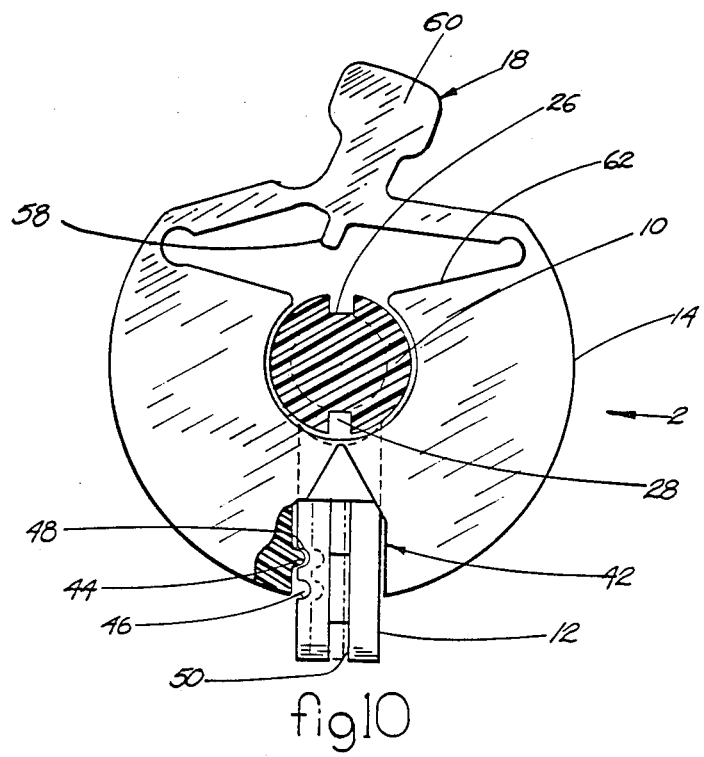
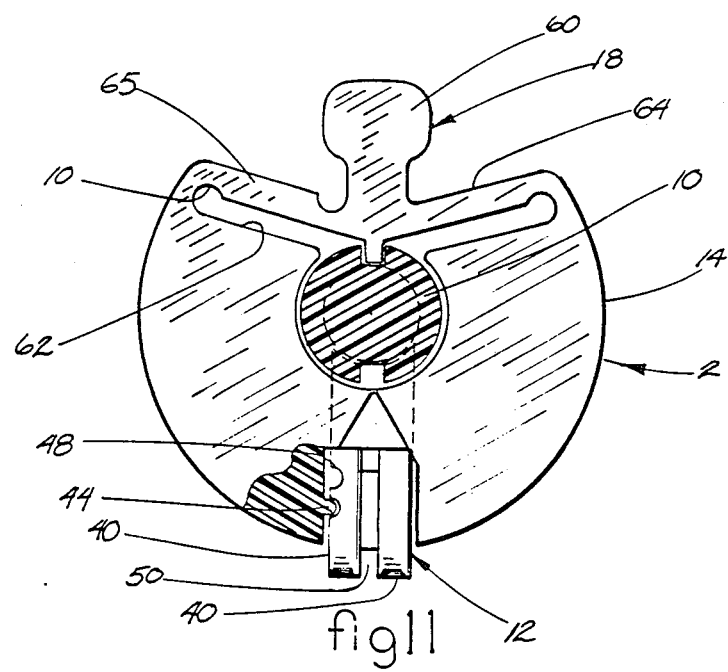

LINEAR AND VERNIER-TYPE SYRINGE

BACKGROUND OF THE INVENTION

Syringes are widely used to administer drugs or other substances, to withdraw body fluids, or to dispense liquids for a variety of medical and other purposes. A syringe typically comprises a cylinder, a piston that is reciprocable in the cylinder and protrudes from an open end thereof, and a needle attached to the other end of the cylinder. Almost universally, such syringes are currently mass produced from a low-cost material, e.g. by molding the syringe and the piston from plastic materials such as polypropylene. The needle is made of a suitable material such as surgical steel and includes an adapter so that it can be attached to the the syringe.

For many applications, a conventional syringe, which has a plunger that reciprocates linearly in the syringe, is sufficient because there is no need to precisely control the amount of liquid that is drawn into or ejected from the syringe.

At other times, however, a precise control of the amount of liquid leaving or entering the syringe is necessary for reasons of health, cost of the dispensed liquid or otherwise. A syringe having a manually operated, linearly reciprocable piston cannot provide this control. Instead, such applications require syringes in which the piston is moved in the cylinder in precisely controlled increments, e.g. a Vernier-type syringe. Typically, such syringes are relatively complicated to construct and maintain. Moreover, the person using the syringe, e.g. a physician should have both types of syringes available to be prepared for any eventuality that may arise. When this is not the case complications may arise at the critical moment when the syringe is needed.

A further complicating factor is that syringes which permit a precise metering of the amount of liquid that is dispensed are relatively costly. Unlike conventional syringes, they are not normally throwaway items. Instead, they must be cleaned and sterilized after each use. Thus, a physician, for example, either requires a supply of several such syringes or he can use a single such syringe only at spaced time intervals, i.e. after a used syringe has been cleaned and sterilized. The former alternative is cumbersome in practice and relatively expensive; the latter alternative is undesirable and in certain situations, such as when a physician makes a number of calls at the same time, outright unacceptable.

To overcome this dilemma, applicants have disclosed in a commonly owned co-pending patent application an adapter to convert low-cost conventional, throwaway syringes into a Vernier-type syringe by substituting an exteriorly threaded piston for the conventional piston of the syringe, or by appropriately modifying the latter so that it has an exterior thread. Further, a mechanism is attached to the open end of the syringe which can engage the piston thread and requires that the piston be rotated about its axis to reciprocate it in the cylinder.

The present invention extends the concept disclosed in the co-pending patent application. As in the co-pending application, the present invention makes it possible to use a syringe in two modes. First, it can be used by conventionally linearly reciprocating the piston in the cylinder, hereinafter usually referred to as the "linear mode". Second, it can be used by requiring that the piston be rotated about its axis to reciprocate it in the syringe, hereinafter usually referred to as "Vernier mode". Additionally, the syringe can be operated incrementally by rotating the piston as in the Vernier mode but generating a signal each time the piston has rotated through a predetermined arc, hereinafter sometimes referred to as the "incremental mode". However, the present invention does not employ an adapter to convert a conventional syringe into a Vernier syringe. Rather, it provides a syringe which is both, i.e. which has the three alternative operating modes without, however, requiring a separate adapter that must be fitted to the syringe.

SUMMARY OF THE INVENTION

A syringe assembly (hereinafter usually referred to simply as a "syringe") constructed in accordance with the present invention can be used in all three modes, i.e. by linearly reciprocating the piston in the cylinder or by rotating it continuously or incrementally about its axis to move it in an accurately controllable manner into and out of the cylinder. The piston has an external thread that extends over at least a portion of its length. The cylinder includes an arm which protrudes laterally from the periphery of the cylinder. It can be hinged relative to the cylinder so that a free end of the arm, fitted with a piston thread engaging section, can be extended through a cutout in the syringe into the interior thereof. The head includes a section adapted to engage the piston thread at a point located a short distance from the open end of the cylinder. Further, the syringe includes a locking mechanism to retain the thread section on the arm in engagement with the piston thread so that the two cannot become accidentally disengaged and the syringe cannot unintentionally change from its Vernier mode of operation to its linear operating mode.

A further aspect of the present invention tactically and/or audibly signals to the user of the syringe each time the piston, when it is operated in its Vernier mode, has been rotated about its axis through a predetermined arc, i.e. each time the piston has moved a predetermined linear increment in the cylinder and a corresponding, predetermined volume of liquid has been ejected from (or drawn into) the cylinder.

In a preferred embodiment of the invention, this is accomplished by fitting the exterior of the piston with one or more longitudinal grooves and biasing a detent into engagement with the piston periphery so that a tactile and/or audio signal is generated each time the detent engages the groove and a corresponding predetermined volume of liquid has been ejected from the cylinder. To permit disengagement of the detent from the piston, for example when the piston is to be operated in its linear mode, the detent is mounted to a bi-stable, over-center membrane which positions the detent in a first, operative position (in which the detent is biased against the piston and the syringe is operated in its incremental mode) or a second, inoperative position in which the detent is retracted and positioned away therefrom.

The cylinder, the arm hingeably attached thereto and the detent can be injection molded in one piece from thermoplastic polymer materials, such as polypropylene, for example. Thus, aside from an injection mold which is initially slightly more expensive, the cost of a cylinder is substantially the same as the cost of a conventional syringe cylinder. Similarly, the piston is preferably injection molded from a thermoplastic polymer material such as polypropylene and its cost is again substantially the same as the cost of an injection molded conventional piston except for the slightly higher initial cost of the injection molding tooling.

Since the cost of a mold is normally amortized over approximately one million parts, and since the amount of plastic material required for molding the syringe and the piston of the present invention is at most negligibly greater than that required for prior art cylinders and pistons, the cost of a syringe constructed in accordance with the present invention is about the same as the cost of prior art syringes. Yet, unlike prior art syringes, the syringe of the present invention can be operated in any of the three operating modes.

The changeover from one mode to the Vernier mode requires no more than a quick pull or push on the hingeably movable arm to release or engage it from the piston thread. The change to the incremental mode requires only a push on the detent to engage it with the piston periphery. Both operations are substantially instantaneously performed.

Thus, the present invention provides a syringe at a cost of no more than comparable prior art syringes which can be operated in one of the available modes without requiring tedious adjustments, the change of parts, tools or time-consuming activities such as finding the type of syringe which is "right" for the task at hand. Consequently, it is expected that the syringe of the present invention may capture a major portion of the worldwide demand for syringes.

In addition, the syringe of the present invention can be more efficiently packed, shipped and stored since the piston of the present invention also serves as a package for the hypodermic needle. To facilitate the latter it is preferred to form a longitudinally extending cavity in the end of the piston which is disposed outside the syringe during use. This cavity is dimensioned so that the needle for the syringe can be placed into the cavity and is frictionally retained therein during storage and shipment.

When the syringe of the present invention is packed, it defines a kit comprising only three parts; the cylinder, including its integral mode selector and signaling device forming a first part, the piston forming a second part, and the needle, disposed within the cavity in the piston, forming a third part. The labor required to assemble the kit is minimal and automatable; all that is necessary is to place the needle inside the piston cavity, place the piston (containing the needle) into the cylinder, placing the cylinder inside the package, sealing the package, and sterilizing the packaged syringe assembly in the prescribed manner and prevent contamination of the syringe. The elimination of five separate needle packaging steps further contributes to the overall cost efficiency of the syringe assembly of the present invention.

BRIEF DESCRIPTION OF THE DRAWINGS

FIG. 10 is an enlarged view, in section, is taken on line 10—10 of FIG. 3, and illustrates the setting of the syringe for operation in its linear mode;

FIG. 11 is a plan view, in section, is taken on line 11—11 of FIG. 9, and illustrates the setting of the syringe for operating it in its Vernier mode;

DESCRIPTION OF THE PREFERRED EMBODIMENTS

Figure 1:
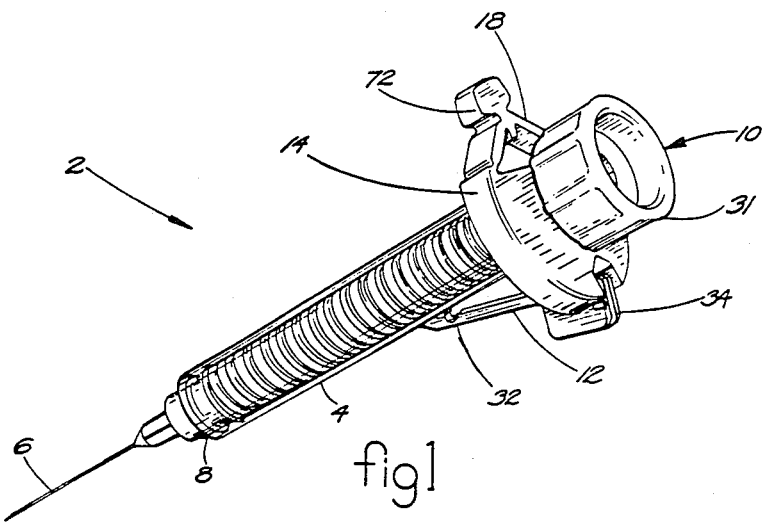
FIG. 1 is a perspective view of a syringe constructed in accordance with the present invention which is set to operate in its linear mode.

Referring to FIGS. 1–3 and 10, a syringe 2 constructed in accordance with the present invention generally comprises an elongated cylinder 4, a needle 6 attached to a first end 8 of the cylinder and a piston 10 reciprocably disposed in the cylinder. The cylinder includes an operating mode selector 12, to select the operation of the syringe in its linear mode or its Vernier mode, a collar 14 at an open end 16 of the cylinder and a signal generator 18, for operating the syringe in its incremental mode, which signals to the user of the syringe when a metered, predetermined volume of liquid has been ejected from (or drawn into) the syringe cylinder.

The cylinder 4 of the syringe assembly is injection molded, preferably from a transparent, semi-transparent or translucent plastic material, as is well-known in the art, and may include the customary volume graduations 20 on its exterior. The end 8 of the cylinder is conventionally formed to lockingly engage needle 6.

Figures 2, 3:
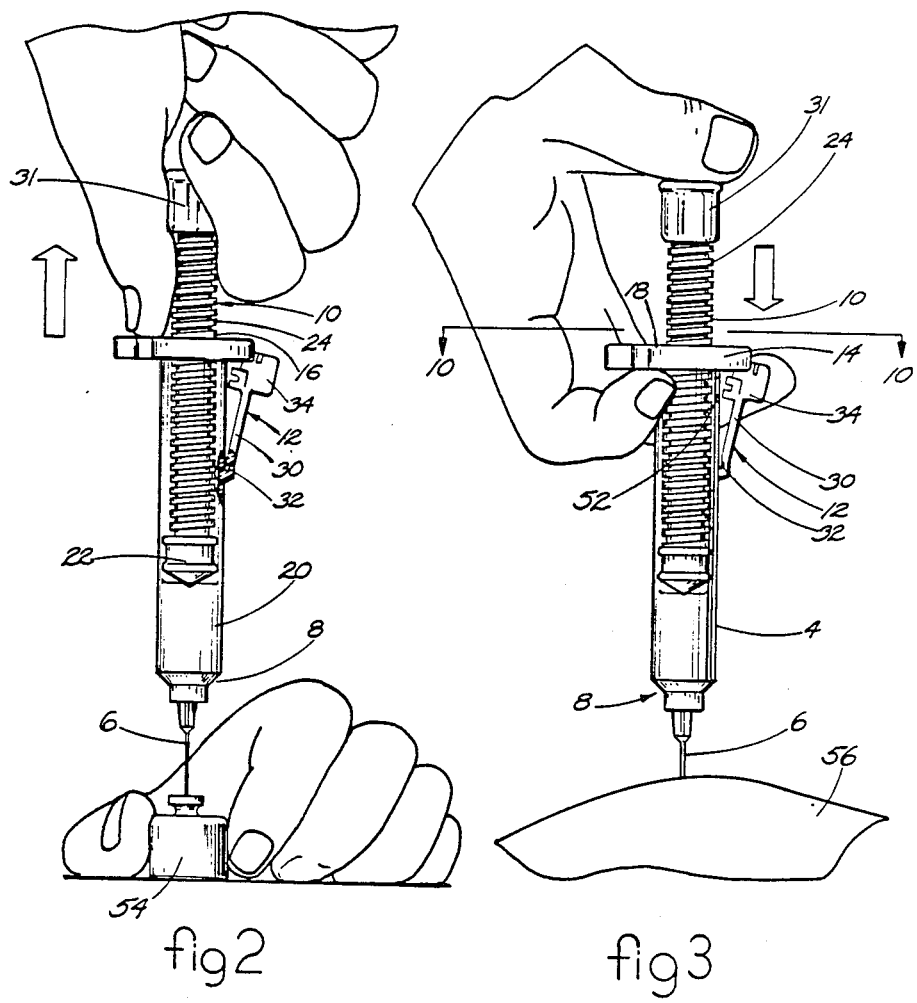
FIGS. 2 and 3 are side elevational views of the syringe shown in FIG. 1 and illustrate the operation of the syringe by linearly moving the piston proximally within the cylinder to draw liquid into or distally to eject liquid from the cylinder, respectively.

Piston 10 extends through open cylinder end 16 so that it can reciprocate in the cylinder and collar 14 is dimensioned so that a user can grasp it and singlehandedly, linearly push the piston into the cylinder, for ejecting liquid through needle 4 (as illustrated in FIG. 3) or pull the piston out of the cylinder, to draw liquid into the cylinder (as illustrated in FIG. 2). Collar 14 has a sufficient thickness so that it is relatively rigid and does not deflect under the forces applied by the user when operating the syringe in its linear mode.

Piston 10 is elongated and generally cylindrical and includes a gasket 22, such as a rubber boot or O-rings, at its end disposed inside the cylinder. The gasket sealingly engages the interior walls of the cylinder and prevents the escape of liquid in the cylinder past the gasket when the piston is actuated.

The piston further has an exterior thread 24 of a pitch selected as will be further described below which extends over the full, or at least a substantial portion of the length of the piston. A pair of longitudinal, axially extending, linear grooves 26, 28 are formed on the exterior of the piston, extend over the length of thread 24, and are equally spaced 180° from each other. The free end of the piston may be provided with a knob 30 to facilitate the operation of the piston by pulling or pushing it linearly, during the linear operating mode of the syringe, or rotating it about its axis during operation of the syringe in its Vernier mode. The exterior diameter of the piston, including the threads, is slightly less than the interior diameter of the syringe to assure its unimpeded movement into and out of the cylinder.

The operating mode selector 12 is defined by an arm 30 which protrudes laterally from the periphery of cylinder 4 at a point 32 spaced some distance from open cylinder end 16. The arm is integrally constructed, i.e. injection molded with the cylinder and is, therefore, made of the same plastic material as the cylinder. Preferably, it is injection molded while the arm protrudes transversely from the cylinder periphery, e.g. at an angle of up to about 90°. The plastic material at the point 32 where the arm is joined to the cylinder is maintained sufficiently thin so that the arm can be pivoted relative to the cylinder about an axis which is approximately tangent to the cylinder periphery and perpendicular to the longitudinal axis of the cylinder.

The free end of the arm defines a head 34 which includes at least one and preferably two piston thread engaging sections 36 facing towards the cylinder when head 34 is proximate the open cylinder end 16, i.e. it faces in a counterclockwise direction as illustrated in FIGS. 2 and 3. The forward ends of the thread sections includes a curvature 38 which is complementary to the curvature of thread 24 on piston 10 so that the thread sections of the head can engage substantially the full depth of the piston threads. A pair of spaced apart tabs 40 form part of head 34 and project from arm 30 in a direction opposite from thread sections 36. The tabs have a sufficient size so that they can be conveniently grasped by a user between his thumb and index finger and they are spaced apart so that they are readily forced together as illustrated in dotted lines in FIG. 10.

Collar 14 includes a guide groove 42 of a width so that it can slidably accommodate head 34. Further, arm 30 has a length and head 36 is shaped so that the head is disposed within and guided by groove 42 when it is proximate the open cylinder end 16, i.e. in the upwardly inclined position shown in FIGS. 2 and 3, for example. One of the sides of groove 42 includes a protrusion 44 and the face of the adjacent tab includes a pair of spaced apart grooves shaped and located to cooperate with protrusion 44 so that when the aft groove 46 engages the protrusion, thread sections 46 are disposed interiorly of the cylinder and engage piston thread 24. The forward groove 48 is positioned so that when it is engaged by protrusion 44 the thread sections 36 of the head are disengaged from piston thread 24.

The tabs 40 define between them a gap 50 which is wider than the height of protrusion 44 in guide groove 42 of the collar. Preferably the gap width exceeds the protrusion height by a substantial amount so that the protrusion readily disengages from the tab grooves 46, 48 when the user compresses the tabs to hingeably move head 34 from one position to the other, or to withdraw it from guide groove 42 altogether.

To enable thread sections 36 and portions of tabs 40 proximate thereto to extend into the interior of cylinder 4 and engage piston threads 24, the cylinder includes a cutout 52. It extends from the free cylinder end 16 coextensively with guide groove 42 in collar 14 to below the collar a distance sufficient to permit entry of both thread sections 36 into the cylinder Turning now to the operation of syringe 2 and referring to FIGS. 1–6, 10, 11, 18 and 19, with piston 10 inserted in cylinder 4 as shown in FIGS. 2 or 3, for example, and with forward groove 48 of tab 40 engaged by protrusion 44, syringe 2 is ready for use in its linear operating mode. To draw liquid into the cylinder, needle 6 is inserted in a liquid container, such as a vial 54, and piston knob 30 is grasped by the user and pulled away from the cylinder as indicated by the arrow in FIG. 2 until the desired volume of liquid has been drawn into the cylinder. The liquid is ejected from the cylinder by grasping the underside of collar 14 with the index and middle fingers, for example, and pushing against piston knob 30 with the thumb to move the piston towards the cylinder as is indicated by the arrow in FIG. 3. This movement of the piston ejects liquid from the cylinder and out of the needle into a body part 56, for example.

Figure 4:
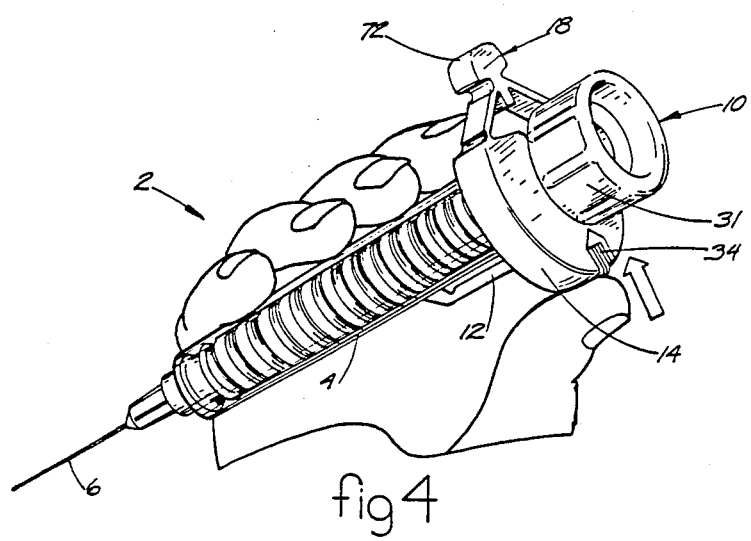
FIG. 4 is a perspective view of the syringe similar to FIG. 1 set to operate in its Vernier mode.
Figures 5, 6:
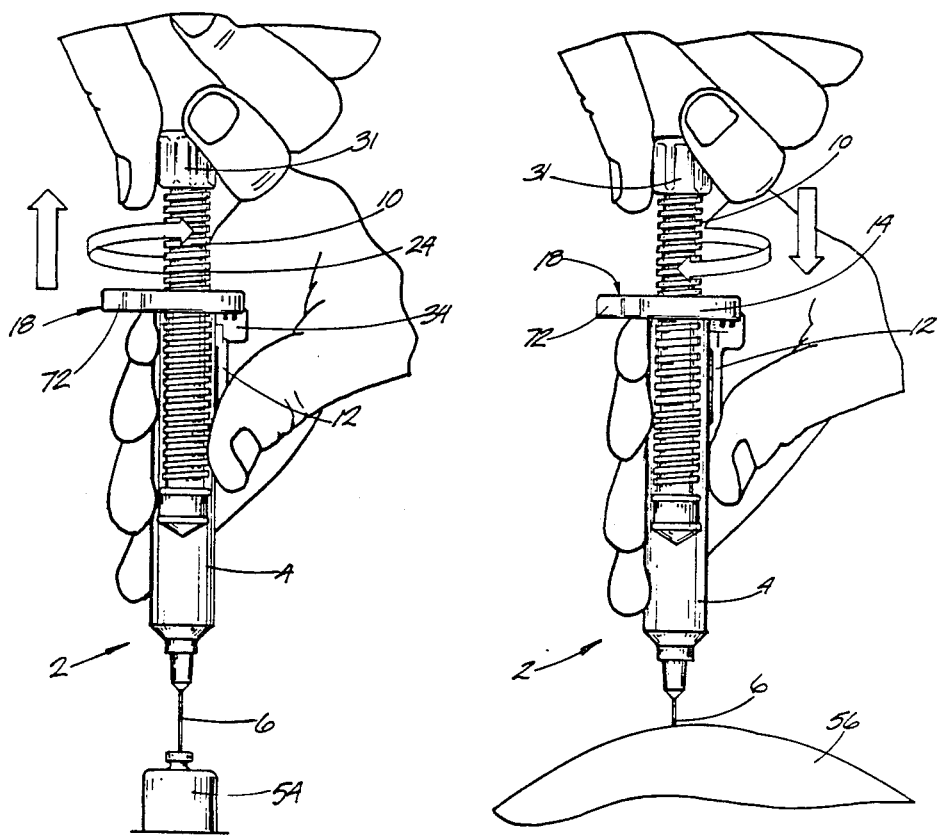
FIGS. 5 and 6 are side elevational views of the syringe shown in FIG. 4 and illustrate the manner in which liquid is drawn into, or ejected from, the cylinder, respectively, by rotating the piston about its axis to in turn produce proximal or distal axial movement.
Figure 7:
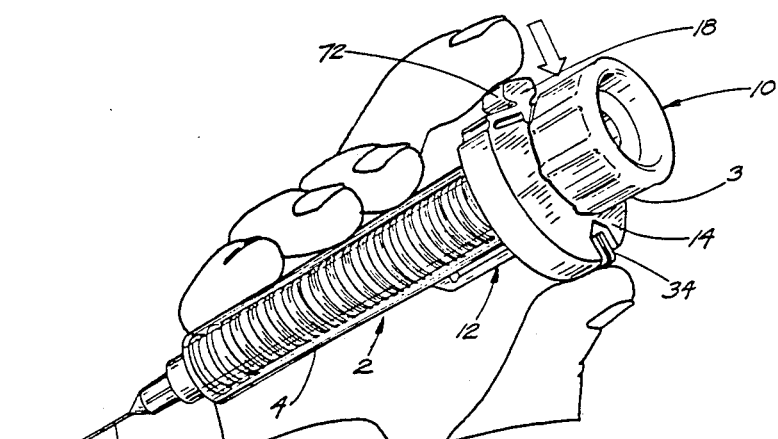
FIG. 7 is a perspective view of the syringe similar to FIG. 4 and shows the syringe set to operate in its Vernier mode and additionally to incrementally signal to the user the amount of liquid drawn into or ejected from the syringe.
Figure 8:
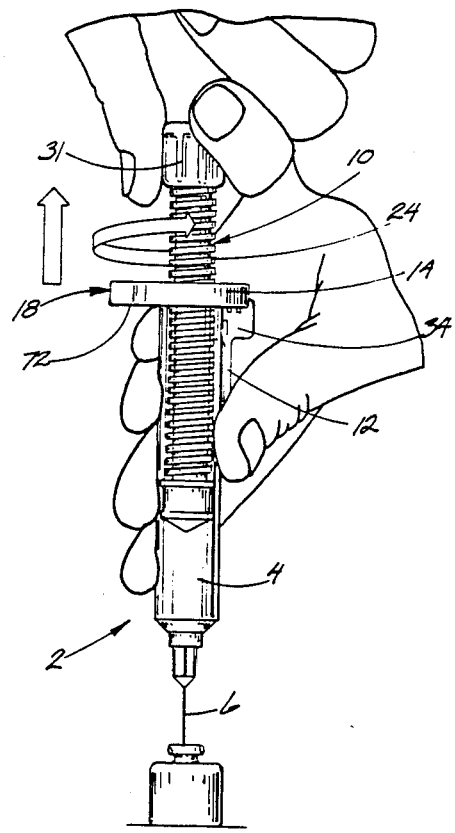
FIGS. 8 and 9 are side elevational views of the syringe shown in FIG. 7 and illustrate the operation of the syringe to incrementally draw liquid into or incrementally eject liquid from the cylinder, respectively, by rotating the piston about its axis.
Figure 9:
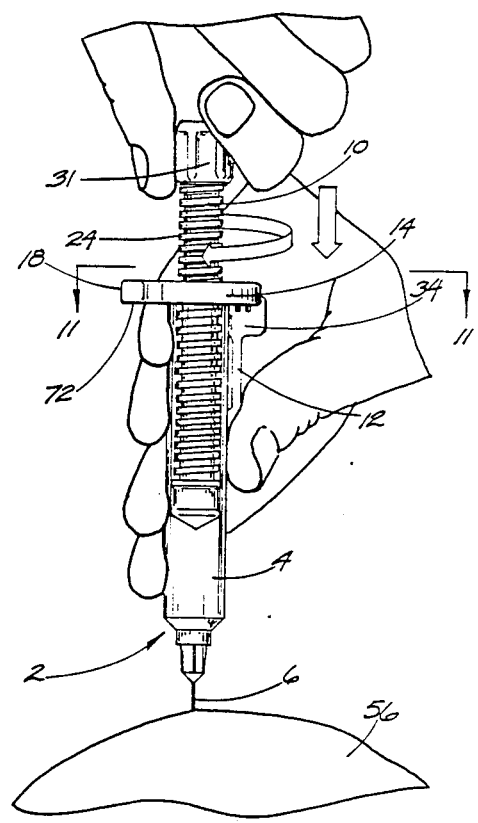

The operating mode of the syringe 2 can be changed from its linear mode (illustrated in FIGS. 1–3) to its Vernier mode, illustrated in FIGS. 4–6, by initially grasping tabs 40 of head 34 between the thumb and index fingers and compressing the tabs, as illustrated in FIG. 10, for example, to disengage protrusion 44 on collar 14 from the forward groove 48. The head is then hingeably moved towards the piston, so that the thread sections 36 engage piston thread 24, until collar protrusion 44 is aligned with aft groove 46 in tab 40. Upon the release of the tabs they resiliently return to their normal position, protrusion 44 engage groove 46 and head 34 is locked in its Vernier mode position It is now impossible to operate the syringe in its linear mode. Instead, the syringe is operated by rotating piston 10 about its axis. When piston thread 24 is righthanded, the piston is moved out of the cylinder, to draw liquid from vial 54 through needle 6 into the cylinder, by rotating it in a counterclockwise direction as indicated by the curved arrow in FIG. 5. Conversely, liquid is ejected from the syringe by grasping piston head 30 and rotating it in a clockwise direction as illustrated by the curved arrow in FIG. 6.

To facilitate a precise metering of the liquid drawn into or ejected from the syringe, the pitch of piston thread 24 is selected so that one full revolution of the piston about its axis moves the piston in a linear direction in the cylinder over a length which ejects a predetermined volume, e.g. 0.5 cc or another convenient volumetric measurement.

To operate syringe 2 in its incremental mode, it preferably also includes signal generator 18 to indicate to the user when the piston has been rotated through a predetermined arc, e.g. through one-half of one full revolution, to facilitate the precise metering the amount of liquid ejected from the syringe. Referring to FIGS. 4-11, the signal generator is formed by a detent 58 which forms a ridge that is parallel to and adapted to engage piston groove 26 and the periphery of piston 10 when biased towards it.

In the preferred embodiment of the invention, the piston includes two longitudinal grooves 26, 28 which are equally spaced from each other by 180°. Thus, each time a groove passes beneath biased detent 58, the detent drops into the groove. This temporarily increases the resistance against further rotation of the piston about its axis and generates a tactile sensation which indicates to a user how much liquid has been ejected from or drawn into the cylinder. In addition, the detent generates a clicking sound, or audio signal, which is also sensed by the user.

In the presently preferred embodiment of the invention, collar 14 includes a radially open cutout 62 which has the shape of a sector, is located diametrically opposite from guide groove 42 for the head 34 of the operating mode selector, and provides access in a generally radial direction to the portion of the piston disposed within the axial extent of collar 14. The detent is mounted to and projects radially inward towards the piston from first and second arms 64, 63 which meet at their adjoining ends, from where the detent 58 projects, and which have outer ends joined to the remainder of collar 14 in the vicinity of its periphery. The width of the arms and the length of the ridge of detent 58 equal the thickness of collar 14 and the combined length of arms 64, 65 exceeds the shortest (i.e. straight line) distance between the attachment points of the arms to the collar. The arms are sufficiently flexible to function as a bi-stable membrane which has a first, operative position (shown in FIG. 11), in which the arms are inclined inwardly towards the piston and detent 58 is biased into engagement with the periphery of the piston. The membrane has a second stable, inoperative position (shown in FIG. 10) in which the arms extend outwardly, away from the piston, and detent 58 is out of contact with the piston periphery.

Thus, when the syringe is operated in its Vernier mode and the membrane is in its inoperative position, the syringe is operated by rotating the piston about its axis. However, no signals are generated which indicate to the user when the piston has been rotated about a predetermined arc and a corresponding predetermined volume has been ejected from the syringe. Conversely, when the membrane is in its operative position and the detent is biased against the piston periphery, the detent drops into the piston groove(s) 26 (28) each time one passes beneath the detent. This generates the above-described tactile and/or audio sensation when the syringe is to be operated in its incremental mode.

To facilitate movement of the membrane between its two operative positions, the signal generator further includes a button 72 which projects from arms 64, 65 in an outward direction. It is readily grasped by a user to pull the membrane from its operative to its inoperative position or to push it from its inoperative to its operative position.

To minimize the cost of the syringe, which is an important feature of the present invention, the arms 64, 65, detent 58 and button 72 are integrally constructed, e.g. injection molded with the collar so as to eliminate the need for handling individual parts and subsequently assembling them. For the same reason, collar 14 is integrally constructed, i.e. injection molded with the cylinder 4. It should be understood, however, that the benefits of the present invention are also attained by constructing the one-piece cylinder described in the preceding paragraphs of individual components which are suitably assembled by bonding, riveting, welding or the like should costs be of no concern or for other reasons such as an unavailability of the required injection mold.

Figure 14:
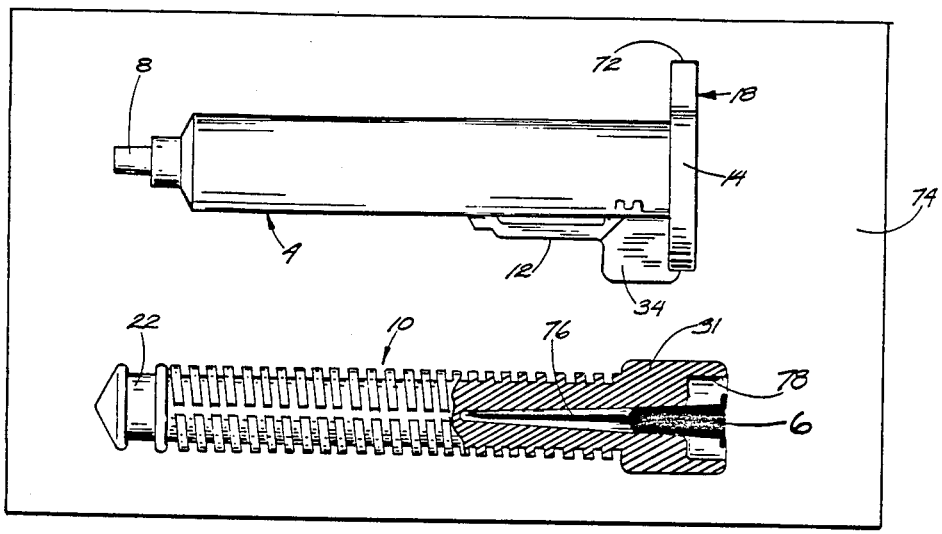
FIG. 14 is a plan view of a syringe kit constructed in accordance with the present invention and packaged for storage and shipment.
Figure 15:
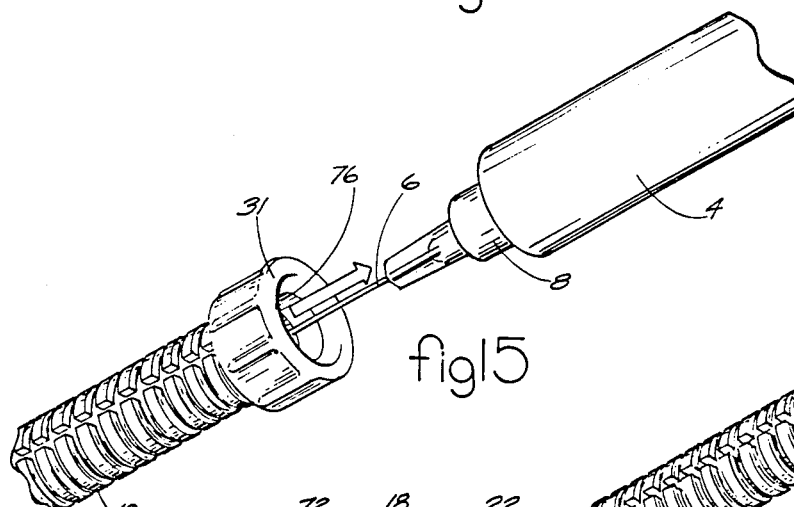
FIG. 15 is a fragmentary, exploded, side elevational perspective view and illustrates the first step for assembling the kit shown in FIG. 4 into an operative syringe by attaching the needle to an end of the syringe cylinder in a non-contaminating manner.
Figure 16:
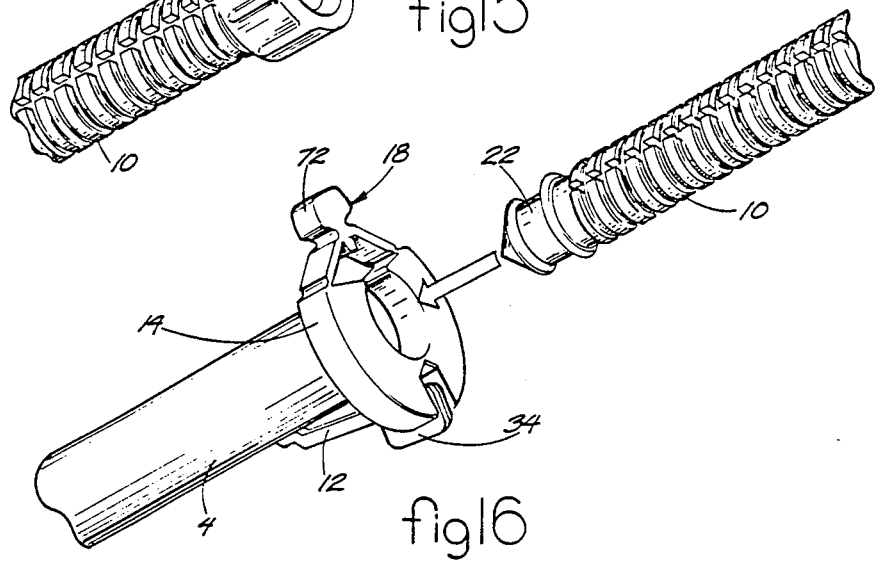
FIG. 16 is a fragmentary, side elevational view and illustrates the second step for assembling the kit of FIG. 14 into a operative syringe by linearly moving the piston into the syringe cylinder.
Figure 17:
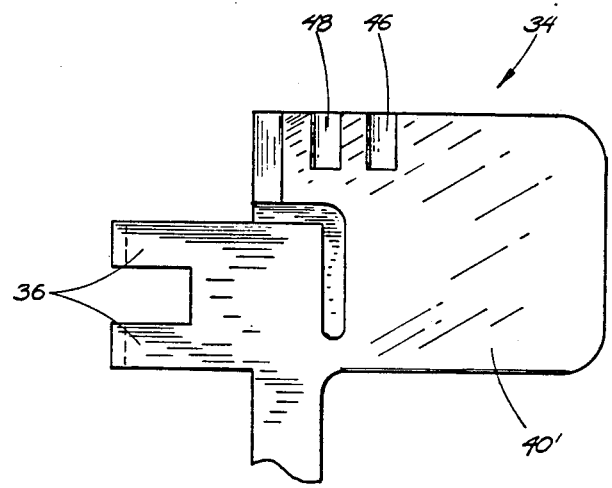
FIG. 17 is an enlarged, fragmentary, side elevational view of a hingeably mounted, piston thread engaging arm forming part of the operating mode selector.
Figure 18:
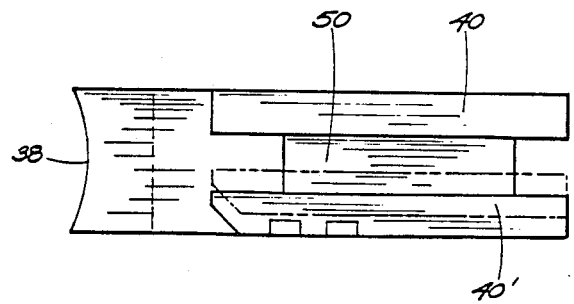
FIG. 18 is a plan view of the arm shown in FIG. 17.

Referring now to FIGS. 14-16, syringe 2 of the present invention essentially comprises three separate parts, i.e. cylinder 4, needle 6 and piston 10 The three parts are typically assembled at the point and time of actual use. Between manufacture and use the syringe is shipped and stored by placing the three components in a package 74, such as a blister package, for example, which hermetically seals the components against contamination. To facilitate this packaging, storage and shipment of the syringe, piston 10 includes an elongated cavity 76 which extends in a generally axial direction from the exterior end of the piston defined by knob 31. The cavity has a length so that substantially the entire needle is disposed therein. Its outer section 78 is enlarged to accommodate the structure of the needle which is locked to the cylinder during use. The cavity in general and the outer section 78 thereof in particular are dimensioned so that it frictionally engages the needle and retains the needle inside the cavity during storage and shipment in package 74.

When the syringe is to be used, the package is opened and cylinder 4 is axially aligned with piston 10 holding needle 6 in its cavity 76 so that the needle end 8 of the cylinder faces the piston cavity. The cylinder and the piston are then moved towards each other to slip the end of the needle onto the cylinder and lock it thereto as is conventional. The needle is then withdrawn from the cavity by moving the cylinder axially away from the piston as is indicated by the arrow in FIG. 15. It will be noted that this application of the needle to the cylinder does not require that the needle be touched by the user. Thus, its sterility is maintained.

Thereafter the positions of the cylinder and the piston are inverted so that the piston end with gasket 22 is axially aligned with open cylinder end 16. The piston is then moved into the cylinder in an axial direction as indication by the arrow in FIG. 16. During this operation, the head 34 of the operating mode selector 12 must be in its linear mode position, in which the thread section 36 is disengaged from piston thread 24 because if the head were in its Vernier mode position the thread sections protruding into the cylinder would prevent the axial insertion of the piston.

Figure 12:
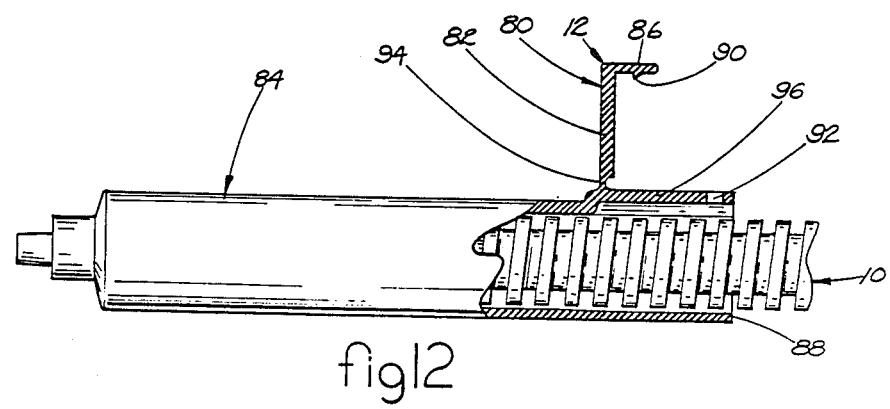
FIG. 12 is a fragmentary, side elevational view, partially in section, and illustrates another embodiment of the present invention for changing the operating modes of the syringe and illustrates it in the linear operating mode.
Figure 13:
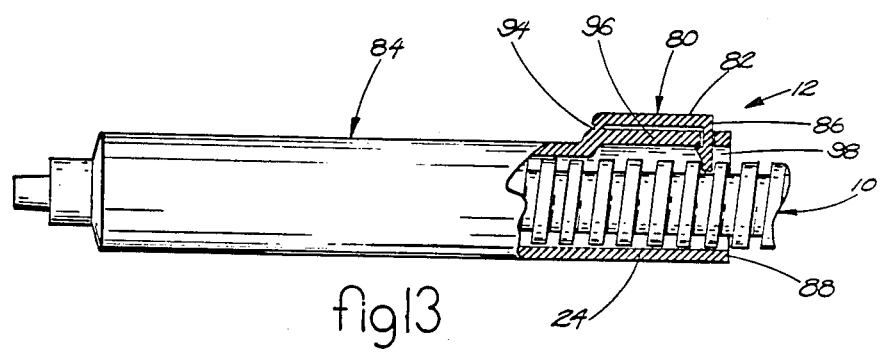
FIG. 13 is a fragmentary, side elevational view, partially in section, of the syringe shown in FIG. 12 and illustrates it in its Vernier operating mode.

Another embodiment of the present invention is illustrated in FIGS. 12 and 13. It differs from the embodiment described above primarily in the construction and functioning of the operating mode selector 12 Specifically, in this embodiment, the mode selector is defined by a generally L-shaped arm 80 the long leg 82 of which projects laterally, e.g. perpendicularly from the periphery of a syringe 84. The short leg 86 of the arm extends towards open syringe end 88 and includes a catch or tooth 90 spaced some distance from the free end of the short leg. The syringe includes a generally radially oriented cutout 92 proximate to but spaced from its free end which is dimensioned so that the short leg, including tooth 90 can be extended therethrough by pivoting arm 80 about a point 94 at which it joins the cylinder.

To accommodate the positioning of tooth 90 interiorly of the syringe when the short leg 86 extends through cutout 92 (shown in FIG. 13), a short section 96 of the syringe contiguous with its open end 88 on the side where arm 82 protrudes from the cylinder is widened outwardly to space this section from the periphery of piston thread 24.

The syringe 84 illustrated in FIGS. 12 and 13 is operated in its linear mode by positioning the arm 80 so that the short leg 86 is outside syringe cutout 92. In this position of the arm the piston can be linearly reciprocated in the syringe in the same manner as was described above.

When the syringe is to be operated in its Vernier mode, arm 80 is pivoted about point 94 until the short leg 86 extends through cutout 92 and tooth 90 is disposed interiorly of cylinder wall section 96. The cutout is positioned relative to the L-shaped arm so that it slightly biases the short leg 86 away from hinge point 94. As a result thereof, as soon as tooth 90 clears the cylinder cutout, it snaps back towards the hinge point, engages wall section 96 and thereby locks the L-shaped arm into its closed position illustrated in FIG. 13. The free end of the short leg 86 now defines a thread section 98 which engages the piston thread, prevents linear axial movements of the piston in the cylinder and forces the user to rotate the piston about its axis to move it into or out of the cylinder in the same manner as was described above.

The embodiment of the invention shown in FIGS. 12 and 13 is particularly adapted for non-reusable syringes because once tooth 90 engages the cylinder, it is not readily releasable. Although the syringe is usable in both the linear and the Vernier modes, as described in the preceding paragraph, once in the Vernier mode, it is not readily returned to its linear mode.

In all other respects, the syringe illustrated in FIGS. 12 and 13 is constructed and functions like the syringe illustrated in FIGS. 1–11. Thus, cylinder 84 is again injection molded and the L-shaped arm 80 of the operating mode selector 12 is integrally molded with the cylinder, typically while the arm protrudes laterally, e.g. up to 90° from the cylinder as is illustrated in FIG. 12. Moreover, to facilitate hingeable movements of the L-shaped arm, the cross-section of the arm in the vicinity of connection point 94 is reduced, as is best shown in FIG. 12.

Further, the cylinder preferably includes a signal generator (not shown in FIGS. 12–13) which cooperates with one or more longitudinal grooves (not shown in FIGS. 12–13) on the periphery of piston 10 so that a tactile and/or audio signal is generated each time the piston is rotated about its axis through a predetermined arc. Still further, the free piston end (not shown in FIGS. 12–13) includes a knob to facilitate the operation of the syringe and a cavity which extends axially into the piston and which is formed and dimensioned to frictionally retain the needle (not shown in FIGS. 12–13) of the syringe while packaged in disassembled form during shipment and storage prior to the use of the syringe.

We claim:

1. A syringe assembly comprising an elongated cylinder having an end adapted to receive a needle, a piston adapted to reciprocate within and sealingly engage the cylinder and having a thread extending over at least a portion of its length, a thread section formed to engage the piston thread, movement means permitting movement of the thread section into engagement with the piston thread, the threaded section and the movement means being integrally formed with the cylinder, and releasable lock means cooperating with the thread section and the cylinder to prevent the unintentional disengagement of the thread section from the piston thread, the lock means including first and second, spaced apart members, and means for applying a force to the members which biases the members towards each other to permit the disengagement of the thread section from the piston thread while the members are biased towards each other, whereby the syringe assembly can be operated by linearly moving the piston in the cylinder while the thread section is disengaged from the piston thread and by rotating the piston about its axis when the thread section engages the piston thread.

2. A syringe assembly according to claim 1 wherein the cylinder, the thread section and the movement means are constructed of a common moldable material.

3. A syringe assembly according to claim 1 wherein the movement means permits hingeable movement of the thread section relative to the cylinder.

4. A syringe assembly according to claim 1 wherein the lock means further includes release means permitting the disengagement of the thread section from the piston thread in response to the application of a force to the release means.

5. A syringe assembly according to claim 4 wherein the release means comprises first and second, spaced apart members, and means for applying a force to the members which biases the members towards each other to permit the disengagement of the thread section from the piston threads while the members are biased towards each other.

6. A syringe assembly according to claim 1 including signaling means cooperating with the cylinder and the piston and signalling to a user of the syringe assembly when the piston has been moved relative to the cylinder to displace a predetermined volume defined by an interior space of the cylinder.

7. A syringe assembly according to claim 6 wherein the signaling means includes means for generating a tactile sensation when the piston has been moved to displace the predetermined volume.

8. A syringe assembly according to claim 7 wherein the signaling means includes means for momentarily increasing the force required to move the piston when the predetermined volume has been displaced.

9. A syringe assembly according to claim 7 wherein the signaling means includes means for generating an audible sensation when the piston has been moved to displace the predetermined volume.

10. A syringe assembly according to claim 6 wherein the signaling means includes selector means for optionally placing the signaling means into an operative position, in which it generates a signal when the piston has been moved to displace the predetermined volume, and an inoperative position in which movement of the piston generates no signal.

11. A syringe assembly according to claim 10 wherein the signaling means comprises an indentation in an exterior of the piston and a detent and over-center arms on the cylinder biasing the detent into one of its operative and inoperative positions.

12. A syringe assembly according to claim 11 wherein the over-center arms and the detent are integrally constructed with the cylinder.

13. A syringe assembly according to claim 11 wherein the indentation includes at least one axial groove on the exterior of the piston which extends over at least a portion of the axial length of the piston thread, and wherein the detent is constructed and positioned to engage the groove each time it passes the detent during rotation of the piston about its axis.

14. A syringe assembly according to claim 13 including first and second, equally spaced axial grooves on the exterior of the piston for engagement by the detent, whereby the detent generates a signal each time the piston is rotated about its axis through an arc of 180°.

15. A syringe assembly according to claim 1 wherein the piston has a first end disposed interiorly of the cylinder during operation of the syringe assembly and a second end disposed exteriorly of the cylinder, and wherein the piston further includes an axially oriented cavity extending from the second end towards the first end, the cavity being shaped to frictionally engage and retain the needle within the cavity during storage and shipment.

16. A syringe assembly comprising a cylinder constructed of a moldable material and having a first end adapted to receive a needle and a second, generally open end; arm means hingeable relative to the cylinder about an axis substantially perpendicular to an axis of the cylinder and pivotable between a first position in which the arm means is generally transverse to the cylinder and a second position in which it is generally parallel to the cylinder; the arm means including a free end positioned so that it is proximate the second cylinder end when the arm means is in the second position; the free end including a thread section facing towards the cylinder axis when the arm means is in its second position; the cylinder including a cutout permitting the thread section to penetrate into the cylinder; an externally threaded piston reciprocable in the cylinder having a first end disposed within the cylinder and a second end disposed exteriorly thereof; the thread section being formed so that it engages the piston thread when the arm means is in its second position; lock means for selectively locking the arm means in its second position so that reciprocating piston movements within the cylinder are only possible by rotating the piston about its axis, the locking means including first and second, resilient, spaced apart members defined by one of the cylinder and the arm means, and means defined by the other one of the syringe and the arm means and cooperating with the spaced apart members for constraining the arm means in its second position so long as the members are spaced apart, and means permitting the members to be moved resiliently towards each other so as to permit movement of the arm means from its second towards its first positions to thereby disengage the thread section from the piston thread; and means for signaling when the piston has rotated about its axis through a predetermined arc; whereby the syringe assembly can be operated by linearly reciprocating the piston in the cylinder while the arm assembly is in its first position and by rotating the piston about its axis when the arm assembly is in its second position.

17. A syringe assembly according to claim 16 wherein the cylinder includes a collar proximate its second end.

18. A syringe assembly according to claim 17 wherein the collar defines a radially open cutout, and including a bi-stable detent disposed in the cutout, and being movable between a first position in which the detent is relatively remote from the piston and a second position in which the detent is resiliently biased into engagement with a periphery of the piston, and wherein the piston includes a depression on its exterior positioned so as to be engaged by the detent when the detent is in its second position and the piston is rotated about its axis, whereby the engagement of the piston exterior by the detent generates at least one of a tactile sensation and an audible sensation each time the detent engages the depression.

19. A syringe assembly according to claim 18 wherein the depression is defined by at least one longitudinally oriented groove extending over substantially the full axial length of the piston thread.

20. A syringe assembly comprising a cylinder having a first end adapted to receive a needle and a second, open end, arm means protruding from the cylinder at a point spaced from the respective ends of the cylinder and formed so that the arm means can be hingedly moved relative to the cylinder, the arm means having a free end remote from the cylinder, a piston reciprocably movably disposed in the cylinder and including an external thread extending at least over a substantial portion of the piston length and at least one longitudinally oriented groove on an exterior of the piston and extending over a substantial portion of the axial length of the piston thread, a collar disposed proximate the second cylinder end and extending over only part of the circumference of the cylinder so as to define a generally radially oriented cutout in the collar, a membrane extending across the cutout, located radially outward of the piston, attached to the collar and having a length greater than the shortest distance between points of attachment to the collar so that the membrane has bi-stable positions proximate to and spaced from the piston, detent means carried by the membrane and formed to engage the longitudinal groove in the piston in one of the bi-stable positions of the membrane, the free end of the arm means including a thread section formed and arranged to engage the piston thread when the arm means is moved to a position in which its free end is proximate the piston, the free end further including first and second, resilient, spaced apart tabs and the cylinder including lock means lockingly engaging the tabs when the thread section engages the piston thread and releasing the tabs when they are biased towards each other so as to release tabs from the lock means and permit movement of the free arm end away from the piston to disengage the thread section from the piston thread, whereby the syringe assembly can be operated by moving the piston linearly relative to the cylinder while the thread section is disengaged from the piston thread and the piston can be reciprocated in the cylinder only by rotating it about its axis when the thread section engages the piston thread and the tabs are engaged by the lock means, and whereby further the positioning of the membrane in its stable position in which the detent is relatively proximate the piston generates at least a tactile sensation each time the groove on the piston is engaged by the detent during rotation of the piston about its axis.

21. A syringe according to claim 20 including means operatively connected with the detent means for manually moving the detent means between its bi-stable positions.

22. A syringe according to claim 21 wherein the arm means is integrally constructed with the cylinder of a common material.

23. A syringe assembly according to claim 22 wherein the collar is integrally constructed with the cylinder of the common material.

24. A syringe assembly according to claim 23 wherein the membrane is integrally constructed with the cylinder of the same common material.

25. A syringe assembly according to claim 24 wherein the detent means is integrally constructed with the cylinder of the common material.

26. A syringe according to claim 20 wherein the collar has a predetermined thickness in the direction of the axis of the cylinder, and wherein the membrane has a width, in the direction in the cylinder axis, which is substantially the same as the thickness of the collar.

27. A syringe assembly according to claim 26 wherein the detent means includes a ridge for engaging the longitudinal groove on the piston, the ridge having a length parallel to the groove substantially equal to the thickness of the collar.

28. A syringe assembly according to claim 20 wherein the tabs are oriented substantially perpendicular to the axis about which the arm means hingeably moves, wherein the free end has a thickness parallel to the hinge axis, and wherein each tab has a thickness which is less than one-half the thickness of the free end.

29. A syringe assembly according to claim 28 wherein the collar defines a guide groove which is substantially perpendicular to the hinge axis and radially oriented with respect to the cylinder axis, the guide groove having a width to accommodate the free end therein, the free end being formed so that a portion thereof is movably disposed within the guide groove when the thread section engages the piston thread.

30. A syringe assembly according to claim 29 wherein the lock means includes at least one protruberance extending in a direction generally parallel to the hinge axis, and a cooperating depression, one defined by the collar and the other defined by the free end so that the positioning of the protruberance in the depression positions the thread section to engage the piston thread.

31. A syringe assembly according to claim 30 wherein the protruberance has an effective height which is less than a spacing between the tabs of the free end.

32. A syringe assembly according to claim 31 wherein the lock means includes at least two depressions cooperating with the protruberance, one of the depressions positioning the free end, when engaged by the protruberance, so that the thread section is disengaged from the piston thread.

33. A syringe assembly comprising a cylinder constructed of a moldable material having a first end adapted to receive a needle and a second, generally open end, a piston reciprocable movably disposed in the cylinder, having an end protruding past the open end of the cylinder, and a thread extending over at least a substantial portion of the piston length, arm means protruding from the cylinder at a point spaced from the respective ends thereof and hingeable about an axis that is substantially tangential to the cylinder, the arm means including a free end defining a thread section formed to engage the piston thread by hingeably moving the arm means relative to the cylinder, a cutout defined by the cylinder permitting the thread section to protrude into the cylinder and piston thread, and lock means carried by the arm means and the cylinder for locking the arm means to the cylinder when the thread section engages the piston thread, the lock means including a tooth and a cooperating edge defined by the cylinder and the arm means, constructed and positioned to lockingly engage each other when the thread section engages the piston thread to prevent movement of the arm means while the tooth and the edge are in engagement, whereby the syringe assembly can be operated by linearly reciprocating the piston in the cylinder while the thread section is disengaged from the piston thread and by rotating the piston about its axis when the thread section is in engagement with the piston thread.

34. A syringe assembly according to claim 33 wherein the arm means is generally L-shaped.

35. A syringe assembly according to claim 34 wherein the first end is defined by a short leg of the L-shaped arm means.

36. A syringe assembly according to claim 33 wherein the arm means is integrally constructed with the syringe and of the same moldable material.

37. A syringe assembly according to claim 36 including means carried by the cylinder adjacent the open end thereof for signaling to a user when the piston has been rotated about its axis through a predetermined arc.

38. A syringe assembly according to claim 37 wherein the signaling means includes means for momentarily increasing the resistance to rotation of the piston about its axis each time it has been rotated about the predetermined arc.

39. A syringe assembly according to claim 33 wherein the arm means is formed and hinged to the cylinder at a point so that the thread section engages the piston thread at a location intermediate the first and second ends of the cylinder.

40. A syringe assembly according to claim 33 wherein the tooth is defined by the arm means and is disposed interiorly of the cylinder when the thread section engages the piston thread, and wherein the cylinder includes a wall which is spaced from the piston by more than a remainder of the cylinder to provide space for the tooth intermediate such wall and the piston.

41. A syringe assembly according to claim 33 including means for selectively releasing the lock means to permit the disengagement of the thread section from the piston thread.

42. A syringe assembly kit comprising a sealed package; a mold-formed cylinder constructed of a plastic material disposed in the package having a first end adapted to receive a needle and a second open end; arm means mold-formed with the cylinder and constructed of the same plastic material, protruding from a periphery thereof and defining a thread section at a free end of the arm means, the plastic material permitting hingeable movements of the arm means relative to the cylinder; a cutout in the cylinder adjacent the second end thereof through which the thread section can be hingeably extended into an exterior of the cylinder; a piston in the package adapted to reciprocably move in the cylinder, having a thread extending over at least a portion of its length and engageable by the thread section when the thread section extends through the cutout into the cylinder and the piston is disposed in the cylinder, whereby axial movement of the piston in the cylinder requires a rotation of the piston about its axis so long as the thread section engages the piston thread and a signaling means for generating a signal when the piston has been moved longitudinally in the cylinder a predetermined amount by rotating it about its axis, the signaling means including detent means and membrane means carrying the detent means mold-formed with the cylinder and constructed of the same plastic material, the membrane bi-stably positioning the detent means in a first position in which the detent means is resiliently biased into engagement with the piston when the piston is disposed in the cylinder and a second position in which the detent means is spaced from the periphery of the piston.

43. A syringe assembly kit comprising a sealed package; a cylinder disposed in the package having a first end adapted to receive a needle and a second, open end; arm means carried by the cylinder, protruding from a periphery thereof and defining a thread section at a free end of the arm means, the arm means being hingeable relative to the cylinder about an axis that is substantially tangential to the cylinder, a cutout in the cylinder adjacent the second end thereof through which the thread section can be extended into an interior of the cylinder when hingeably moved relative to the cylinder, a piston in the package adapted to reciprocably move in the cylinder and having an end formed to protrude past the open end of the cylinder, the piston including an external thread, an exterior, axially oriented groove extending over at least a portion of the external thread, and a cavity formed in the end of the piston, a needle in the package adapted to be received by the first cylinder end, the needle being disposed in the piston cavity, the piston cavity being formed and dimensioned to frictionally engage and retain the needle in the cavity; and signaling means carried by the cylinder, disposed proximate the second end thereof, and including detent means, membrane means carrying the detent means and bi-stably positioning the detent means without disconnection there from in a first position in which the detent means is resiliently biased into engagement with a periphery of the piston when the piston is disposed in the cylinder and a second position in which the detent means is spaced from the periphery of the piston so that, when the section engages the piston thread, rotation of the piston about its axis causes it to move longitudinally relative to the cylinder and the signaling means generates a signal each time the piston has moved longitudinally in the cylinder a predetermined amount.

44. A kit according to claim 43 wherein the cylinder and the arm means are integrally constructed of moldable material.

45. A kit according to claim 44 wherein the membrane means and the detent means are integrally constructed with the cylinder of the same moldable material.

46. A syringe assembly comprising an elongated cylinder having an end adapted to receive a needle, a piston adapted to reciprocate within and sealingly engage the cylinder and having a thread extending over at least a portion of its length, a thread section formed to engage the piston thread, and movement means permitting movement of the thread section into engagement with the piston thread, the threaded section and the movement means being integrally formed with the cylinder, signaling means cooperating with the cylinder and the piston for signalling to a user of the syringe assembly when the piston has been moved relative to the cylinder to displace a predetermined volume defined by an interior space of the cylinder, the signaling means including selector means defined by an indentation in an exterior of the piston and a detent and over-center arms on the cylinder biasing the detent into or away from the indentation for optionally placing the signaling means into an operative position, in which it generates a signal when the piston has been moved to displace the predetermined volume and the detent engages the indentation, and an inoperative position in which movement of the piston generates no signal.

47. A syringe assembly according to claim 46 including lock means cooperating with the thread section and the cylinder to prevent the disengagement of the thread section from the piston thread.

48. A syringe assembly comprising a cylinder constructed of a moldable material and having a first end adapted to receive a needle and a second, generally open end; arm means hingeable relative to the cylinder about an axis substantially perpendicular to an axis of the cylinder and pivotable between a first position in which the arm means is generally transverse to the cylinder and a second position in which it is generally parallel to the cylinder; the arm means including a free positioned so that it is proximate the second cylinder end when the arm means is in the second position; the free end including a thread section facing towards the cylinder axis when the arm means is in its second position; the cylinder including a cutout permitting the thread section to penetrate into the cylinder; an externally threaded piston reciprocable in the cylinder having a first end disposed within the cylinder and a second end disposed exteriorly thereof; the thread section being formed so that it engages the piston thread when the arm means is in its second position; lock means for locking the arm means is in its second position so that reciprocating piston movements within the cylinder are only possible by rotating the piston about its axis; and means for signaling when the piston has rotated about its axis through a predetermined arc; comprising a bi-stable detent attached to the cylinder proximate its second end being movable between a first position in which the detent is relatively remote from the piston and a second position in which the detent is resiliently biased into engagement with a periphery of the piston, and a depression on the exterior of the piston positioned so as to be engaged by the detent when the detent is in its second position and the piston is rotated about its axis; whereby the engagement of the piston exterior by the detent generates at least one of a tactile sensation and an audible sensation each time the detent engages the depression; and whereby the syringe assembly can be operated by linearly reciprocating the piston in the cylinder while the arm assembly is in its first position and by rotating the piston about its axis when the arm assembly is in its second position.

49. A syringe assembly according to claim 48 wherein the lock means comprises first and second, resilient, spaced apart members defined by one of the cylinder and the arm means, and means defined by the other one of the syringe and the arm means and cooperating with the spaced apart members for constraining the arm means in its second position so long as the members are spaced apart, and means permitting the members to be moved resiliently towards each other so as to permit movement of the arm means from its second towards its first positions to thereby disengage the thread section from the piston thread.

50. A syringe assembly kit comprising a sealed package; a mold-formed cylinder constructed of a plastic material disposed in the package having a first end adapted to receive a needle and a second open end; arm means mold-formed with the cylinder and constructed of the same plastic material, protruding from a periphery thereof and defining a thread section at a free end of the arm means, the plastic material permitting hingeable movements of the arm means relative to the cylinder; a cutout in the cylinder adjacent the second end thereof through which the thread section can be hingeably extended into an exterior of the cylinder; and a piston in the package adapted to reciprocably move in the cylinder, having a thread extending over at least a portion of its length and engageable by the thread section when the thread section extends through the cutout into the cylinder and the piston is disposed in the cylinder, whereby axial movement of the piston in the cylinder requires a rotation of the piston about its axis so long as the thread section engages the piston thread; and 1 signaling means for generating a signal when the piston has been moved longitudinally in the cylinder a predetermined amount by rotating it about its axis, the signaling means including detent means and membrane means carrying the detent means mold-formed with the cylinder and constructed of the same plastic material, the membrane bi-stably positioning the detent means in a first position in which the detent means is resiliently biased into engagement with the piston when the piston is disposed in the cylinder and a second position in which the detent means is spaced from the periphery of the piston.

51. A syringe assembly kit according to 1 claim 50 including a needle in the package adapted to be received by the first cylinder end, and wherein an end of the piston includes a cavity extending generally axially over a portion of the piston length, the cavity being formed and dimensioned to retain the needle in the cavity so long as the piston is in the package.

* * * * *